United States Patent [19]

Engebretson

[11] Patent Number: 5,024,224
[45] Date of Patent: Jun. 18, 1991

[54] METHOD OF READOUT OF IMPLANTED HEARING AID DEVICE AND APPARATUS THEREFOR

[75] Inventor: A. Maynard Engebretson, Ladue, Mo.

[73] Assignee: Storz Instrument Company, St. Louis, Mo.

[21] Appl. No.: 239,556

[22] Filed: Sep. 1, 1988

[51] Int. Cl.⁵ ............................................. A61N 1/00
[52] U.S. Cl. ............................... 128/420.6; 128/898; 128/903
[58] Field of Search .............. 128/419 PT, 420.6, 748, 128/903, 898

[56] References Cited

U.S. PATENT DOCUMENTS

| | | |
|---|---|---|
| 3,633,217 | 1/1972 | Lance . |
| 3,771,173 | 11/1973 | Lamb, Jr. . |
| 3,842,440 | 10/1974 | Karlson . |
| 3,919,722 | 11/1975 | Harmison . |
| 3,974,825 | 8/1976 | Normann . |
| 4,143,661 | 3/1979 | LaForge et al. . |
| 4,213,207 | 7/1960 | Wilson . |
| 4,265,252 | 5/1981 | Chubbuck et al. ................ 128/748 |
| 4,357,497 | 11/1982 | Hochmair et al. . |
| 4,358,539 | 1/1983 | Robinson et al. . |
| 4,428,377 | 1/1984 | Zollner et al. . |
| 4,441,210 | 4/1984 | Hochmair et al. . |
| 4,519,401 | 5/1985 | Ko et al. ........................... 128/748 |
| 4,542,532 | 9/1985 | McQuilkin . |
| 4,611,598 | 9/1986 | Hortmann et al. . |
| 4,662,358 | 5/1987 | Farrar et al. . |
| 4,665,896 | 5/1987 | LaForge et al. . |
| 4,666,443 | 5/1987 | Portner . |

OTHER PUBLICATIONS

Pamphlet #SPA-1238, "An Introduction to the Cochlear Implant," Univ. of California, School of Medicine, Dept. of Otolaryngology, Coleman & Epstein Laboratories and Storz Instrument Company, 1984.

Primary Examiner—David Shay
Attorney, Agent, or Firm—Brooks & Kushman

[57] ABSTRACT

The implanted device includes a rectifier circuit which is switched between modes of half wave and full wave rectification in response to the signal to be conveyed. The external device is inductively coupled to the implanted device through a pair of coils, one coil being embedded beneath the skin, forming the primary and secondary windings of a transformer. The external device delivers energy to the implanted device in amounts which vary in accordance with the rectification mode of the implanted device. By monitoring the energy delivered, the external device determines the rectification modes as they are switched and thereby ascertains the signal being conveyed from the implanted device.

8 Claims, 2 Drawing Sheets

FULL-WAVE

CURRENT

HALF-WAVE

CURRENT

METHOD OF READOUT OF IMPLANTED HEARING AID DEVICE AND APPARATUS THEREFOR

BACKGROUND AND SUMMARY OF THE INVENTION

The present invention relates generally to the conveying of signals from a device implanted beneath the surface of the skin to a second device located external to skin. The invention may be used, for example, to convey information from an implantable hearing aid to an external readout device.

The use of implantable devices requires a means for control and programming of the device characteristics from an external signal. In the case of a hearing aid, it may be necessary to set the gain, maximum power output and frequency response after implantation, to provide an optimal setting of parameters for the patient. In this regard, it would be advantageous to provide for the readout of data and parameters from the implanted device.

Control of an implanted device by an external signal can be done by transmitting a modulated carrier signal from an external coil and providing for an internal coil to receive and demodulate the signal. Because the transmitted signal in this case is generated externally, relatively large power sources can be used. Although it is possible to reverse this process to transmit from the implanted device to the external circuitry, it is generally not practical to do so because of the limited power available within the implanted power source.

The present invention provides a solution to this problem in the form of a method and apparatus for transmitting a signal from the implanted device to the external device without requiring an internal transmitter and without requiring excessive power to be consumed by the implanted circuitry. In accordance with the inventive method a signal is conveyed from the implanted device to the external device by modulating the impedance of the implanted device in accordance with the signal to be conveyed and then inductively supplying energy to the implanted device via the external device. By monitoring the energy delivered, the external device ascertains the modulated impedance of the internal device and thereby ascertains the signal being conveyed.

In the presently preferred embodiment the external device employs a class C power amplifier coupled to an external coil. The external coil is placed in close proximity to an implanted coil forming part of the implanted device, thereby defining primary and secondary windings of a transformer. The internal device includes a rectification circuit which can be switched between modes of half wave and full wave rectification in response to the signal to be conveyed. The class C power amplifier delivers power through the transformer defined by the external and internal coils to the implanted rectifier circuit. A current sensing resistor in the power supply of the power amplifier monitors the energy delivered to the rectifier, specifically monitoring the current pulses drawn by the power amplifier. A decoder circuit responsive to the current sensing resistor monitors the frequency of pulses delivered by the class C amplifier and thereby monitors the rectification modes to thereby ascertain the signal being conveyed by the implanted device. If desired, the energy delivered to the rectifier circuit may be used to provide operating power to the implanted device or to charge a suitable energy storage means.

For a more complete understanding of the invention, its objects and advantages, reference may be had to the following specification and to the accompanying drawings.

DESCRIPTION OF THE PREFERRED EMBODIMENTS

Figure 1:
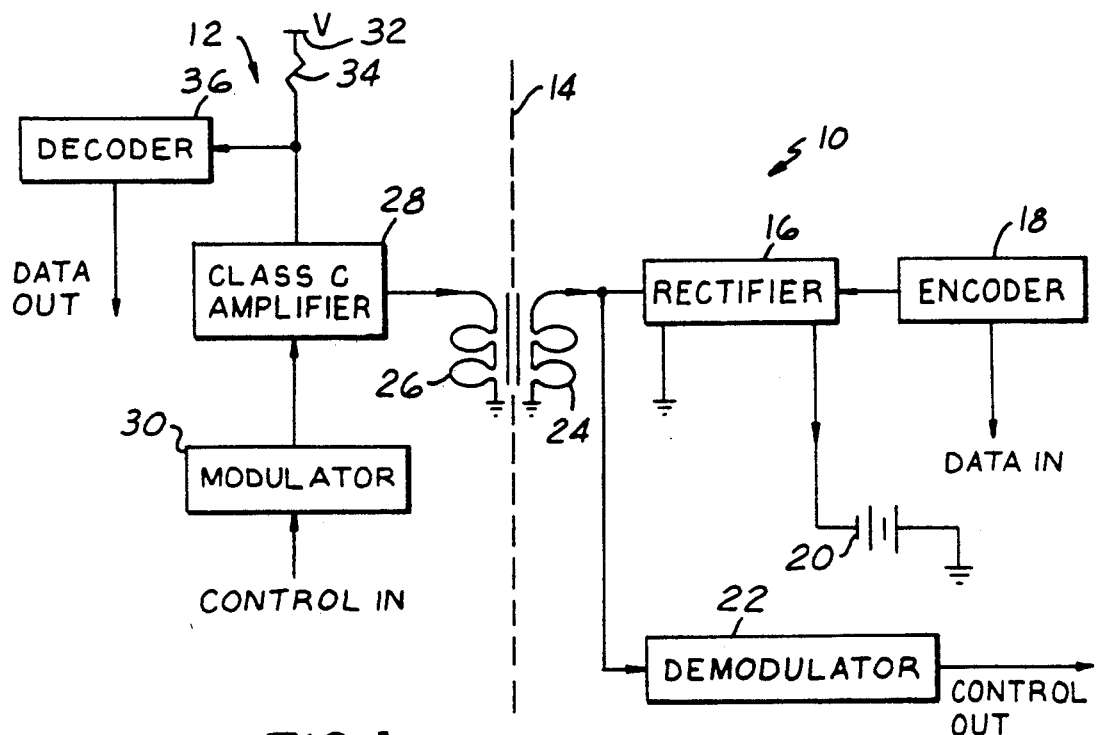
FIG. 1 is a functional block diagram of the invention.

Referring to FIG. 1, a presently preferred embodiment of the invention is illustrated with the implanted device depicted generally at 10 and the external device depicted generally at 12. The surface of the skin of the human patient is depicted by the dashed line 14.

Implanted device 10 comprises a rectifier circuit 16 and an encoder circuit 18 which is connected to control rectifier circuit 16. Rectifier circuit 16 provides an output 18 which may be used to charge an energy storage device such as a rechargeable battery 20. Battery 20 may be connected to the other implanted components to provide operating power for the implanted device. The implanted device may also include a demodulator circuit 22, which, together with rectifier circuit 16, is connected to implanted coil 24. Coil 24 is preferably placed adjacent the skin surface 14 to allow inductive coupling with a corresponding external coil 26 placed adjacent to or in contact with skin surface 14.

The external device of the presently preferred embodiment comprises a class C amplifier 28 with a modulator circuit 30 supplying a control signal used to convey messages from the external device to the implanted device. The class C amplifier 28 supplies current to the external coil 26. By virtue of the inductive coupling between coils 24 and 26, the equivalent of a transformer is created, with coil 26 serving as the primary winding and coil 24 serving as the secondary winding. Class C amplifier 28 delivers energy to the implanted device through this transformer.

Current is supplied to the class C amplifier via the voltage source 32 which includes a current sensing resistor 34. A decoder circuit 36 is connected to current sensing resistor 34 in order to sense and decode changes in the current delivered to amplifier 28 when the circuit is in operation.

Communication from the external device to the implanted device is accomplished by modulating the class C amplifier 28 so that the energy delivered through the transformer comprising coils 24 and 26 carries a modulated signal. This modulated signal is demodulated by demodulator 22. In the presently preferred embodiment, the modulator/demodulator system may be used to convey control signals from the external device to the implanted device. These control signals may, for example, set hearing aid parameters, to allow a hearing aid to be fine-tuned after it has been implanted.

Signals are conveyed from the implanted device to the external device using encoder 18. The signal to be conveyed is supplied to encoder 18 as DATA IN. Encoder 18 causes rectifier 16 to switch selectively between modes of half wave rectification and full wave rectification. The rectification modes may be considered as different binary states and in this fashion binary messages can be represented as changes in the impedance of the implanted device as a function of time.

In this regard, rectifier 16 may be considered as a load on the secondary side of the transformer comprising coils 24 and 26. As amplifier 28 delivers energy through the transformer to rectifier 16, the switching between full wave and half wave rectification modes results in load modulation which determines the amounts of energy flowing from amplifier 28 to rectifier 16 as a function of time. When rectifier 16 is in the full wave rectification mode, amplifier 28 delivers energy in pulses during both half wave segments of the alternating current waveform. When rectifier 16 is in the half wave mode, amplifier 28 delivers energy in only every other half wave segment.

Figure 2A:
FIGS. 2A and 2B are waveform diagrams illustrating exemplary current pulses resulting from the full wave and half wave rectification modes, respectively.
Figure 2A:
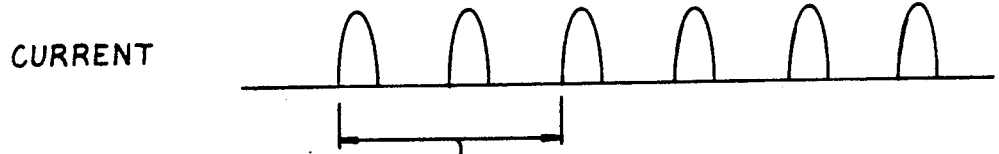
Figure 2B:
Figure 2B:
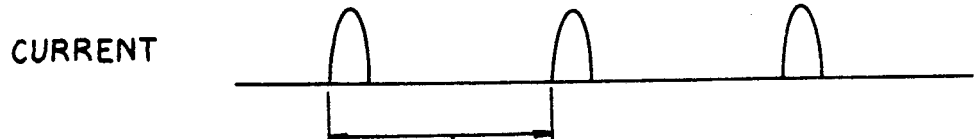

The energy delivered through amplifier 28 to rectifier 16 is sensed by current sensing resistor 34 and decoder 36. Exemplary current waveforms are illustrated in FIGS. 2A and 2B, representing the full wave and half wave modes, respectively. It will be seen that the current flowing through resistor 34 comprises two current pulses per cycle when full wave rectification is in effect and comprises one pulse per cycle when half wave rectification is in effect. This difference in the number of current pulses per cycle is detected by decoder 36 as a representation of the rectifier mode at any given point in time. Since the rectifier mode is controlled by the DATA IN signal applied to encoder 18, decoder 36 provides a DATA OUT signal which is the binary equivalent of the input DATA IN signal. In this fashion the implanted device can convey signals to the external device for providing a readout of the conditions sensed or existing beneath the surface of the skin.

The foregoing embodiment implements a binary signal communication system, which is presently preferred since present day readout equipment is well adapted to handle binary or digital signals. However, the concept of load modulation may be applied to analog systems, as well. For example, rather than simply switching between half wave and full wave modes, the rectifier and encoder may be configured to modulate load in an analog fashion to effect analog changes in the amplitude of energy consumed by the load. The amplitude of energy consumption and not simply the temporal occurrence of energy pulses would then be indicative of the signal being conveyed. In such an application, it may be useful to have a reference level against which the encoded energy consumption level may be compared. One way to implement this is to use a first half cycle of the alternating current waveform as a reference level while applying a modulating load to the second half cycle. On the external device side, the amplitude of the current supplied to amplifier 28 would, in the first half cycle, be indicative of the reference level and, in the second half cycle, the be indicative of the analog signal being conveyed (referenced to the reference level).

The load modulation technique implemented by the invention integrates well with another requirement of many implanted devices, namely the requirement of supplying power to the implanted device. Whether rectifier 16 is in half wave or full wave mode, energy is nevertheless being delivered to the implanted device and may be used to charge an implanted energy storage device such as battery 20. Thus the invention makes it possible to recharge an implanted battery automatically as a benefit of obtaining a readout of conditions beneath the surface of the skin, e.g., previous settings of the implanted hearing aid. The invention when incorporated in an implanted hearing aid thus makes it possible for a doctor to readout a patient's hearing aid parameters and to adjust those parameters if necessary, without any need to perform further invasive surgery.

Figure 3:
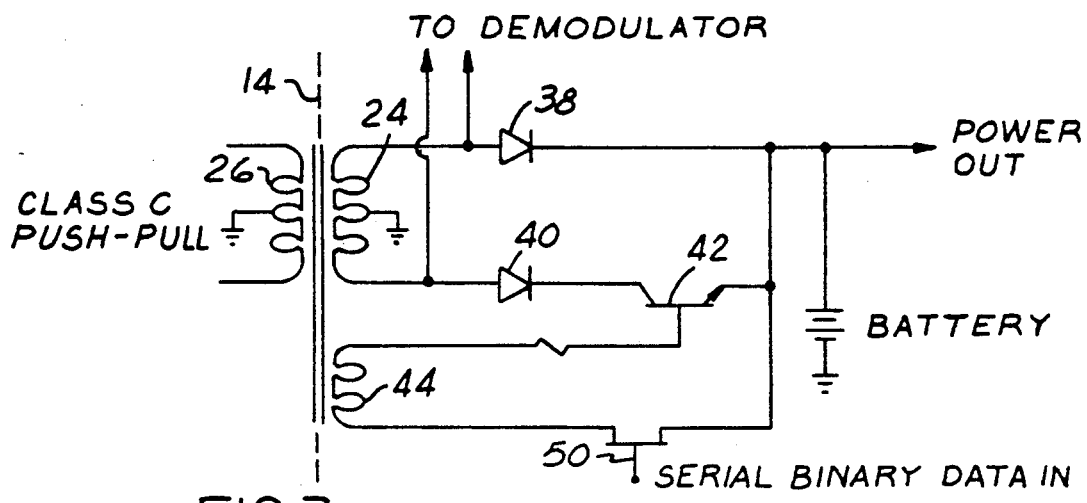
FIG. 3 is a schematic diagram illustrating a first embodiment of switchable rectifier circuit.
Figure 4:
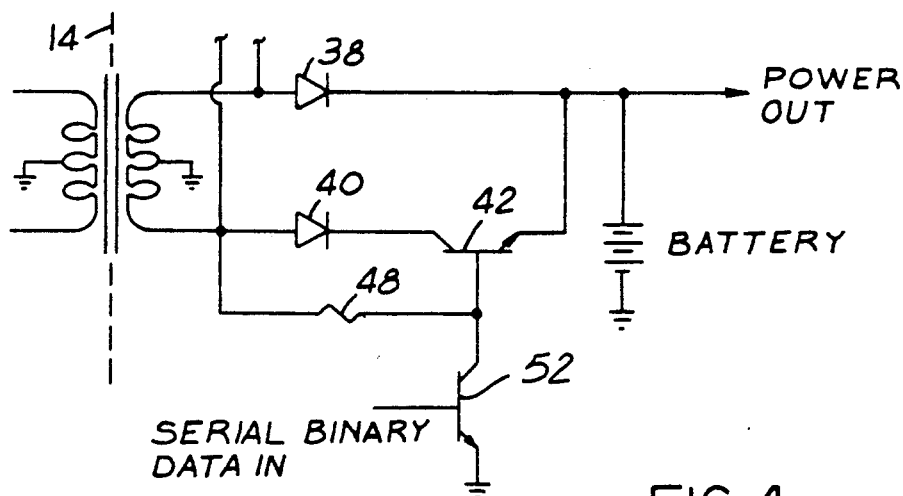
FIG. 4 is a schematic diagram illustrating a second embodiment of switchable rectifier circuit.

FIGS. 3 and 4 depict alternate embodiments of the switchable rectifier circuit 16. Both embodiments employ first and second diodes 38 and 40. Each rectifier circuit acts as a half wave rectifier at all times through diode 38. Both circuits act as a full wave rectifier through diodes 38 and 40, when transistor 42 is turned on in response to serial binary DATA IN. The embodiments of FIGS. 3 and 4 differ in the manner in which transistor 42 is biased.

In the embodiment of FIG. 3 an auxiliary secondary winding 44 is inductively coupled to coils 24 and 26 for biasing transistor 42 through resistor 46. In the embodiment of FIG. 4 transistor 42 is biased through resistor 48 coupled to the secondary coil 26. In the embodiment of FIG. 3 a field effect transistor 50 receives the serial binary data input which causes transistor 42 to switch diode 40 in and out of the rectifier circuit in response to the input data. In the embodiment of FIG. 4 a bipolar transistor 52 is used to receive the serial binary data input and to cause transistor 42 to switch diode 40 into and out of the circuit.

Figure 5:
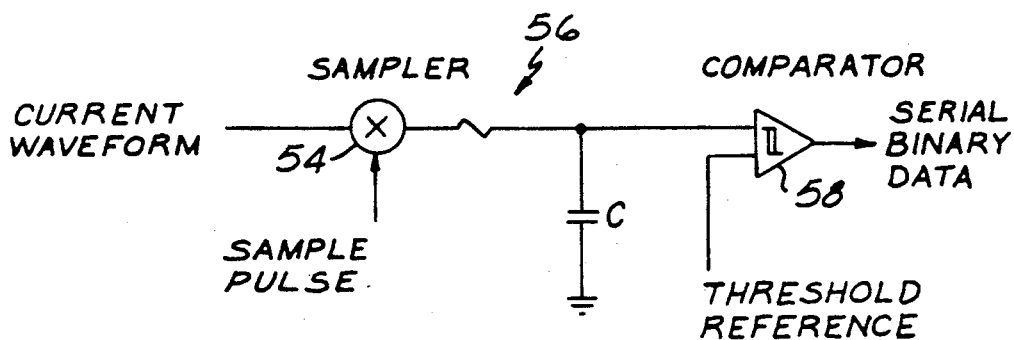
FIG. 5 is a schematic diagram illustrating a suitable decoder circuit.

A suitable decoder 36 is depicted in greater detail in FIG. 5. Decoder 36 employs a pulse driven sampling circuit 54 which periodically samples the current waveform through current sensing resistor 34. The output of sampling circuit 54 is delivered to an RC holding circuit 56 to which a comparator circuit 58 is connected. The comparator circuit senses the sampled current waveform signal being held in RC holding circuit 56. Depending on whether the held value is above or below a threshold reference level, the approprate serial binary data is output from comparator 58.

Sampling circuit 54 receives a sampling pulse wavetrain adapted to cause the sampling circuit to sample the current waveform a sufficient number of times to distinguish between the current waveforms of FIGS. 2A and 2B. Sampling should occur at least once every half cycle in order to detect the presence or absence of a current pulse within a given half cycle.

The method of readout of parameters and data from the implanted device does not require an internal transmitter and does not require excessive power to be consumed by the implanted circuitry. These are advantages which make the invention well-suited for use in implanted hearing aids. The invention is, however, applicable to other implanted medical devices such as pacemakers and the like. While a class C power amplifier is used in the presently preferred embodiment, other energy delivery systems can also be employed.

From the foregoing it will be understood that the present invention provides an advantageous method of communicating between an implanted device and an external device. The invention makes it possible to implement a full duplex serial communication protocol between the implanted device and the external device, so that flexible control, readout of key parameters and self-testing of the implanted system can be achieved.

While the invention has been described in its presently preferred embodiments, the invention is capable of modification or change without departing from the spirit of the invention as set forth in the appended claims.

What is claimed is:

1. A method of conveying signals from a hearing aid with an implanted device having an impedance to a device located external to the body of the implant wearer and inductively coupled to said implanted device, the improvement comprising:

modulating the impedance of said implanted device in accordance with a first signal to be conveyed;

using said externally located device to deliver energy to said implanted device in amounts which vary in accordance with the modulated impedance of said implanted device;

using said externally located device to ascertain the amounts of energy delivered to said implanted device, said amounts of energy being indicative of the modulated impedance of said implanted device;

from said ascertained amounts of energy delivered using said externally located device to ascertain said first signal, whereby said first signal is conveyed from said implanted device to said externally located device;

wherein said first device includes a rectification means switchable between modes of half wave and full wave rectification and wherein said modulating step is performed by using said first signal to cause said rectification means to switch between said modes.

2. A method of conveying a binary signal from a first device implanted beneath the surface of the skin to a second device located external to the skin, comprising:

inductively coupling said first and second devices;

said first device having a rectification means switchable between modes of half wave and full wave rectification;

selectively switching said rectification means between said modes in accordance with said binary signal;

using said second device to deliver energy to said rectification means in pulses of frequency determined by the mode of said rectification means;

using said second device to monitor the frequency of pulses of energy delivered to said rectification means;

from said monitored frequency ascertaining said binary signal, whereby said binary signal is conveyed from said first device to said second device.

3. A method of conveying a signal from a first device having an impedance implanted beneath the surface of the skin to a second device located external to the skin, comprising:

inductively coupling said first and second devices;

modulating the impedance of said first device in accordance with a first signal to be conveyed;

using said second device to deliver energy to said first device in amounts varying in accordance with the modulated impedance of said first device;

using said second device to ascertain the amounts of energy delivered to said first device, said amounts of energy delivered being indicative of the modulated impedance of said first device;

from said ascertained amounts of energy delivered using said second device to ascertain said first signal, whereby said first signal is conveyed from said first device to said second device;

wherein said first device includes a rectification means switchable between modes of half wave and full wave rectification and wherein said modulating step is performed by using said first signal to cause said rectification means to switch between said modes.

4. The method of claim 3 wherein the step of inductively coupling includes inductively coupling said first and second devices as primary and secondary sides of a transformer.

5. The method of claim 3 wherein the step of modulating includes modulating said impedance of said first device using a binary signal.

6. The method of claim 3 comprising the further step of using said energy delivered to said first device to provide operating power to said first device.

7. The method of claim 3 wherein said first device includes an energy storage means and comprising the further step of using said energy delivered to said first device to charge said energy storage means.

8. A method of conveying signals from a hearing aid having an implanted device having an impedance to a device located external to the body of the wearer, the implanted device and the externally located device having means whereby they may be inductively coupled, the improvement comprising:

placing said externally located device in a position to establish inductive coupling with said implanted device;

modulating the impedance of said implanted device in accordance with a first signal to be conveyed;

using said externally located device to deliver energy to said implanted device in amounts which vary in accordance with the modulated impedance of said implanted device;

using said externally located device to ascertain the amounts of energy delivered to said implanted device, said amounts of energy being indicative of the modulated impedance of said implanted device;

from said ascertained amounts of energy delivered using said externally located device to ascertain said first signal, whereby said first signal is conveyed from said implanted device to said externally located device;

wherein said first device includes a rectification means switchable between modes of half wave and full wave rectification and wherein said modulating step is performed by using said first signal to cause said rectification means to switch between said modes.

* * * * *